(12) United States Patent
Jeffords et al.

(10) Patent No.: US 12,262,926 B2
(45) Date of Patent: Apr. 1, 2025

(54) POWER MODULES AND METHODS FOR BONE ANCHOR AND STYLET INSERTION

(71) Applicant: NuVasive, Inc., San Diego, CA (US)

(72) Inventors: Megan Jeffords, San Diego, CA (US); Ryan Woods, San Diego, CA (US); Naomi Kibrya, San Diego, CA (US); Matthew Tobias Jacobs, San Diego, CA (US)

(73) Assignee: Nuvasive, Inc., San Diego, CA (US)

( * ) Notice: Subject to any disclaimer, the term of this patent is extended or adjusted under 35 U.S.C. 154(b) by 598 days.

(21) Appl. No.: 17/454,542

(22) Filed: Nov. 11, 2021

(65) Prior Publication Data

US 2022/0142681 A1 May 12, 2022

Related U.S. Application Data

(60) Provisional application No. 63/173,944, filed on Apr. 12, 2021, provisional application No. 63/112,816, filed on Nov. 12, 2020.

(51) Int. Cl.
*A61B 17/70* (2006.01)

(52) U.S. Cl.
CPC ...... *A61B 17/7082* (2013.01); *A61B 17/7091* (2013.01)

(58) Field of Classification Search
CPC ............ A61B 17/7082; A61B 17/8897; A61B 17/8875; A61B 17/7076; A61B 17/7074; A61B 17/888; A61B 17/8888; A61B 17/8894
See application file for complete search history.

(56) References Cited

U.S. PATENT DOCUMENTS

| | | | | |
|---|---|---|---|---|
| 8,465,491 | B2* | 6/2013 | Yedlicka | A61B 17/1671 606/80 |
| 10,993,729 | B1* | 5/2021 | Aman | A61B 17/1697 |
| 2010/0262127 | A1* | 10/2010 | Schmied | A61B 17/1624 606/1 |
| 2015/0351820 | A1* | 12/2015 | Straslicka | A61B 17/1697 606/169 |
| 2016/0030100 | A1* | 2/2016 | Divincenzo | A61B 17/7082 606/104 |
| 2019/0125421 | A1* | 5/2019 | Smith | A61B 17/8897 |
| 2019/0231447 | A1* | 8/2019 | Ebbitt | A61B 34/30 |
| 2020/0093530 | A1* | 3/2020 | Klausman | A61B 17/1604 |
| 2020/0281608 | A1* | 9/2020 | Sharifi-Mehr | A61B 17/848 |

FOREIGN PATENT DOCUMENTS

EP 2679177 A1 1/2014

OTHER PUBLICATIONS

Partial International Search Report from PCT/US2021/058860 dated Feb. 16, 2022.

* cited by examiner

*Primary Examiner* — Eduardo C Robert
*Assistant Examiner* — Michelle C Green (57) ABSTRACT

Disclosed herein are power modules and methods for insertion of a cannulated bone anchor and a stylet. Power modules disclosed herein are configured to adjustably control insertion of a bone anchor and a stylet under power from a motor. In certain embodiments, the motor may be included in a power hand piece. The power modules disclosed herein may be further configured to releasably couple a power hand piece to a driver for insertion of the bone anchor and stylet into the bone of a subject.

17 Claims, 10 Drawing Sheets

POWER MODULES AND METHODS FOR BONE ANCHOR AND STYLET INSERTION

CROSS REFERENCE TO RELATED APPLICATIONS

The present patent application claims the benefit under 35 U.S.C. § 119(e) of U.S. Provisional Patent Application No. 63/112,816, filed Nov. 12, 2020, and of U.S. Provisional Patent Application No. 63/173,944, filed Apr. 12, 2021, each of which is incorporated by reference herein as though fully set forth.

BACKGROUND OF THE DISCLOSURE

The spine is critical in human physiology for mobility, support, and balance. Spinal injuries can be debilitating or catastrophic to patients. Even small irregularities in the spine can cause devastating pain and loss of coordination.

Surgical procedures are commonly performed to correct problems with displaced, damaged, or degenerated intervertebral discs. A wide spectrum of spinal procedures involves inserting bone anchors. Using a stylet extending beyond the distal tip of the bone anchor to be inserted may facilitate accurate and efficient insertion of the bone anchor.

SUMMARY OF THE DISCLOSURE

Disclosed herein are devices that allow for stylet and bone anchor advancement into bone. The devices disclosed herein can operate in two separate modes under power. In a first mode, i.e., a stylet advancing mode, the stylet can be advanced and/or spin under power at a predetermined speed, e.g., at 1500 revolution per minute (rpm) with a first torque. In a second mode, i.e., a screw mode, a clutch mechanism can be used to control a driver to drive a bone anchor at a speed lower than that in the stylet mode and a second torque that is higher than the first torque. Disclosed herein are a power hand piece and a power module that can be attached to a medical instrument on the proximal end thereof. Any instrument with a proper fitting at its proximal end, e.g., a screwdriver with square flats, can be attached optionally using complementary features on the power module such as, for example, ball detents and/or a mating female square feature. A stylet can be then inserted through the cannulation on the distal end of the medical instrument and through the power module. A trigger on the power module can be pulled to extend the stylet. The trigger can actuate a friction lock optionally using ball bearings, a collet, or a locking canted coil spring to connect the stylet to the drive shaft. Under power, the stylet can be driven at the spin setting of the power hand piece. To switch to the screw mode, the clutch mechanism at the distal end of the instrument can be rotated until a tactile or audio feedback is provided by the device. At this point, the drive shaft can be linked to a planetary gear system to reduce speed of the power hand piece at a predetermined gear ratio, e.g., 5:1, and increase torque. The clutch mechanism in the screw mode may couple the planetary gears to the female square feature to drive the screwdriver.

Disclosed herein are devices that allow for stylet and bone anchor advancement in two separate modes under power. The stylet can be advanced distally under power. A retention feature can automatically lock the stylet. The stylet can be rotationally constrained to the driveshaft to allow the stylet to be rotated at the speed setting of the power hand piece. A trigger on the instrument can be pulled to advance the stylet to a specified depth beyond the tip of the bone anchor and retract the stylet back to be proximal to the bone anchor tip.

Disclosed herein is a quick connect retention feature of the stylet. The quick connect retention feature may allow for stylet to spin at high speed, e.g., 1500 rpm, when used under power, and translate for pedicle screw trajectory planning or pilot hole creation. The quick connect retention feature may allow for the stylet to be loaded into the proximal end of the power module passively for quick connect retention. Pushing the stylet in distally can force the canted coil spring to engage with the groove(s) on the stylet. The input speed of the driveshaft can be directly transferred to the stylet to spin at the same speed. A trigger or lever can be used to push the stylet and a portion of the drive shaft distally to allow for stylet advancement. The stylet may retract back once the pushing force on the trigger is removed.

Disclosed herein, in some embodiments, the stylet includes a proximal portion or component having a cross-sectional shape, e.g., square cross-section, that mates with a cannulation through the driveshaft of the power module, so the stylet can be rotationally constrained. The proximal portion or component may be coupled, e.g., welded, to a k-wire, and may facilitate coupling of the k-wire to the power module. When the power module is driven under power, the stylet is configured to automatically spin at the same speed of a power hand piece simultaneously. An energy biasing element, e.g., a canted coil spring, may be used to engage a groove on the stylet to hold the stylet for use. The groove may be disposed on the proximal portion or component in certain embodiments. Alternatively, the energy biasing element may be used with more than one groove on the stylet. Loading the stylet into a groove may create a permanent lock from tension loading. To remove the stylet, the user can push the stylet distally into a second groove to reorient the energy biasing element to allow for easy removal. The stylet can be loaded into a telescopic driveshaft having, e.g., three pieces, to allow for control of the stylet for extension and/or retraction. Actuation of the trigger may be configured to translate the stylet along the two drive shaft components, which are all rotationally constrained to one another.

Disclosed herein, in some embodiments, are structural elements of the power module that allow for a distal cap to be rotated to either engage or disengage from a drive feature to switch between two independent drive modes. One drive mode can couple a square coupling such as, e.g., a quick connect coupling, to a planetary gear system to drive in a bone anchor, e.g., pedicle screw, at a decreased speed, e.g., about 300 rpm and increased torque, e.g., about 100 inch-pound (in-lb). The second drive mode can decouple the square quick connect from the planetary gear system to drive in a stylet or k-wire at an increased speed, e.g., about 1500 rpm, and decreased torque, e.g., about 20 in-lb. The distal cap on the power module can be translationally fixed to the distal housing or cover via retaining ring(s). Rotating the distal cap may translate a pusher component that is rotationally constrained to the distal cover or housing. Translating the pusher component can allow for engagement with the gear carrier, e.g., via clutch and clutch engagement. Rotating the distal cap in reverse direction may pull the pusher component back to disengage from the gear carrier. Ball detents may be added to provide tactile and audio feedback and retain the clutch mechanism in the two drive modes. A spring can allow the two clutch faces to be automatically aligned and properly engaged when in use.

In accordance with the foregoing summary and following detailed description, in a first aspect of the disclosure, a power module is provided, the power module being configured to adjustably control insertion of a bone anchor and a stylet under power from a motor. The motor may be, e.g., a component of a power handpiece. The power module may comprise a driveshaft operatively coupled to the motor, and configured to rotate at a first speed equal to a speed of rotation of the motor. The drive shaft may be a telescopic drive shaft, and may comprise a first driveshaft member, a second driveshaft member, and a third driveshaft member, wherein the second driveshaft member is translatable relative to the first driveshaft member and the third driveshaft member. A cannula is provided through each driveshaft member. A first energy biasing element is disposed within the cannula of the second driveshaft member, wherein the first energy biasing element is configured to couple to the stylet, thereby locking the stylet translationally and rotationally to the second driveshaft member.

A cover may be disposed over at least a portion of the power module, wherein the telescopic driveshaft is rotatable relative to the cover, and wherein the first driveshaft member and the third driveshaft member are translationally fixed relative to the cover. The cover may be unitarily formed or comprise two or more cover components, which may be affixed to one another, e.g., by a threaded connection, an adhesive, or a weld.

The driveshaft is configured to engage a stylet within the cannula in a first mode of operation, e.g., a stylet advancement mode of operation, thereby causing the stylet to rotate at the first speed of rotation. A stylet trigger may be coupled to the second driveshaft member, wherein upon engagement, the stylet trigger is configured to cause translation of the second driveshaft member in a distal direction relative to the first and the third driveshaft members.

The power module may further comprise a gear system configured to be couplable at a proximal end thereof to the driveshaft, and at a distal end thereof to a medical instrument, e.g., a screw driver, wherein each of the gear system and the medical instrument include an axially extending cannula through which at least a portion of the stylet extends. The gear system may comprise a sun gear that is configured to be couplable to a distal end of the driveshaft, and to rotate at the first speed of rotation; a gear carrier configured to couple with the sun gear and to rotate at a speed slower than the first speed; one or more planet gears configured to be carried by the gear carrier and to rotate about an axis fixed on the gear carrier; and a ring gear disposed about the gear carrier and the one or more planet gears, wherein each of the one or more planet gears rotates at the slower speed on the ring gear on an inner surface of the cover. A first clutch, i.e., a drive clutch, may be configured to engage with the gear carrier; and a second clutch corresponding to aspects of the distal cap may be configured to axially translate relative to the first clutch and to releasably engage with the first clutch. One or more bearings may be disposed between the cover and the gear system, or between the cover and the driveshaft.

In the first mode of operation, the gear system is configured to be disengaged from the driveshaft, e.g., the second clutch is configured to translate distally and to be disengaged from the first clutch. In the second mode of operation, e.g., a screw advancement mode, the gear system is configured to engage with the driveshaft. In particular, the second clutch is configured to translate proximally and to engage with the first clutch. The first clutch, the second clutch, gear carrier, and the medical instrument are rotationally fixed to one another. This causes a reduction from the input first speed of rotation of the driveshaft to an output second speed of rotation that is lower than the first speed, such that the medical instrument is configured to rotate at the second speed of rotation.

A distal cap may be provided, which is configured to rotatably engage with the second clutch, thereby causing the power module to shift between the first mode of operation and the second mode of operation. The distal cap is configured to be rotatable relative to the cover in a first direction, thereby causing the second clutch to translate distally and to disengage from the first clutch, thereby configuring the device to operate in stylet advancement mode. The distal cap is further configured to be rotatable relative to the cover in a second, opposite direction, thereby causing the second clutch to translate proximally and to engage with the first clutch, thereby configuring the device for operation in screw mode. A quick connect coupling may further be provided, that is configured to reversibly couple a proximal end of the medical instrument to the second clutch, wherein the medical instrument is rotationally fixed to the second clutch when the proximal end of the medical instrument is coupled to the second clutch.

According to a second aspect of the disclosure, a power module is provided, the power module being configured to adjustably control insertion of a bone anchor and a stylet under power from a motor, the power module comprising: a telescopic driveshaft comprising a cannula therein, the cannula being configured to engage the stylet; and a quick connect feature configured to releasably couple the power module to a power handpiece comprising the motor. The quick connect feature comprises: an outer shaft having a lumen therein; and an inner shaft disposed within the lumen of the outer shaft. The inner shaft comprises a first diameter along a length of the inner shaft, a second, larger diameter at a distal end of the inner shaft, and a tapered portion providing a transition from the first diameter to the second diameter. The tapered portion may be smoothly or continuously tapered, or may include curved and/or shouldered surface features. The outer shaft may further include a tapered retention clip configured to releasably couple the proximal end of the stylet to a distal end of the outer shaft.

Further features of the power module include a first groove disposed on an inner surface of the cannula within the telescopic driveshaft; a corresponding groove in the outer shaft; and at least one ball bearing disposed within the lumen of the outer shaft, adjacent the tapered portion of the inner shaft. In the connected position, the at least one ball bearing extends radially outward through the second, corresponding groove in the outer shaft, into the first groove in the telescopic driveshaft, thereby locking the outer shaft in axial engagement with the telescopic driveshaft. In the disconnected position, the inner shaft is configured to translate in a distal direction, thereby causing the at least one ball bearing to move radially inward along the tapered portion and to exit the first groove and the second corresponding groove, thereby releasing the axial engagement of the outer shaft and the telescopic driveshaft.

In a third aspect of the disclosure, the features of the first and second aspects may be combined in a single device including features described with respect to the first aspect as well as features described with respect to the second aspect.

In a fourth aspect of the disclosure, a system is provided for bone anchor insertion which includes a power module connected, e.g., by a quick connect feature, with a power hand piece. The power module may include a stylet management unit, a speed reducing unit, and a drive mode switch unit. A quick connect unit may further be provided for reversibly coupling the power module to a screw driver. The system may further include a stylet inserted within the power module and the bone anchor as described herein, and the bone anchor to be inserted.

In a connected position, the outer shaft is configured to engage a portion of the telescopic driveshaft and a proximal end of the stylet within the cannula; and in a disconnected position, the outer shaft is configured to disengage from the telescopic driveshaft and the proximal end of the stylet.

These and other aspects, advantages and salient features of the invention will become apparent from the following detailed description, which, when taken in conjunction with the annexed drawings, where like parts are designated by like reference characters throughout the drawings, disclose embodiments of the invention.

It is noted that the drawings of the disclosure are not necessarily to scale. The drawings are intended to depict only typical aspects of the disclosure, and therefore should not be considered as limiting the scope of the disclosure. In the drawings, like numbering represents like elements between the drawings

DETAILED DESCRIPTION OF THE DISCLOSURE

Aspects of the present disclosure include devices and modules configured for use in procedures involving the insertion of bone anchors, e.g. cannulated bone anchors, and stylets disposed therein.

As disclosed herein, the term bone anchor is used interchangeably with, and is considered equivalent to, and synonymous with the terms: bone fastener, fastener, fixation screw, spinal fixation screw, bone screw, pedicle screw, and other terms known in the art. The term driver is used interchangeably with, and is considered equivalent to, and synonymous with a screw driver, or any device that drives insertion of a bone anchor as would be understood by one skilled in the art. The term stylet is used interchangeably with, and is considered equivalent to, and synonymous with the terms, k-wire, guide wire, and wire. Use of the term proximal refers to the direction away from attachment of an element to the subject, shown in the figures as direction P (e.g., FIG. 1), while use of the term distal refers to the direction opposite the proximal direction and toward attachment of an element to the subject, shown in the figures as direction D (e.g., FIG. 1).

Figure 1:
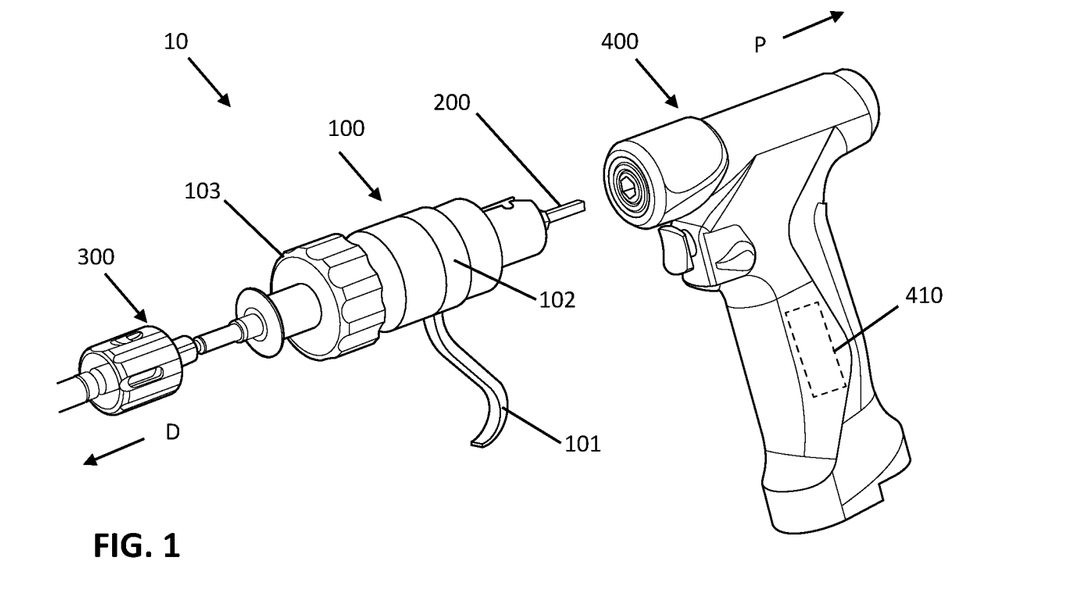
FIG. 1 shows a perspective view of a system including a power module, a power hand piece, a stylet, and a screwdriver, according to embodiments of the disclosure.

With reference to the figures, a power module is disclosed herein, for insertion of a cannulated bone anchor, and a stylet disposed within a cannulated feature of the bone anchor. FIG. 1 illustrates power module 100 in the context of bone anchor and stylet insertion system 10. Power module 100 is configured to be coupled to power hand piece 400 at the proximal end of power module 100. Power handpiece 400 may include a motor 410 configured to drive axial rotation at an output speed. Power module 100 may be configured to couple to driver 300 at a distal end of power module 100, for insertion of stylet 200 and bone anchor 500 (FIGS. 6A-6E) into the bone of a subject.

Figure 2:
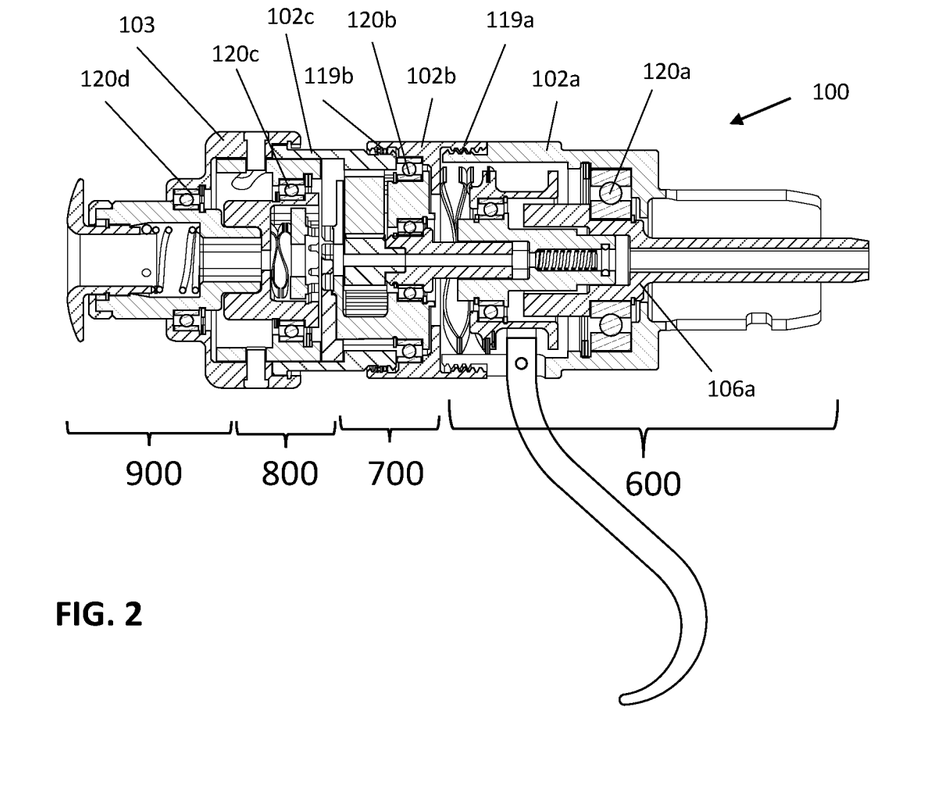
FIG. 2 shows a cross-sectional view of a power module as shown in FIG. 1, according to embodiments of the disclosure.

As shown in FIG. 2, power module 100 may include one or more of stylet management unit 600, speed reducing unit 700, drive mode switch unit 800, and quick connect unit 900. In some embodiments, power module 100 may also include a housing or cover 102 enclosing stylet management unit 600, speed reducing unit 700, and drive mode switch unit 800, in whole or in part with respect to each unit, within a lumen of the cover 102. In various embodiments, cover 102 may be unitarily formed, or cover 102 may be formed of two or more cover components. For example, cover 102 may be made up of first cover component 102a, second cover component 102b, and in some embodiments, a third cover component 102c, each of which may be configured to be coupled together, e.g., by complementary male and female threaded connections, by another complementary connection as known in the art, or the use of adhesive or welding. In the exemplary embodiment depicted in FIG. 2, first cover component 102a covers at least a portion of stylet management unit 600. Second cover component 102b is configured to be coupled at coupling 119a to a distal end of first cover component 102a, e.g., by mating engagement of complementary threaded connectors, welding, adhesive, or other means. Second cover component 102b may be further configured to couple at coupling 119b in a similar manner at a distal end thereof to a proximal end of third cover component 102c. Cover 102 may further be configured to couple with distal cap 103, discussed further herein.

Figure 4:
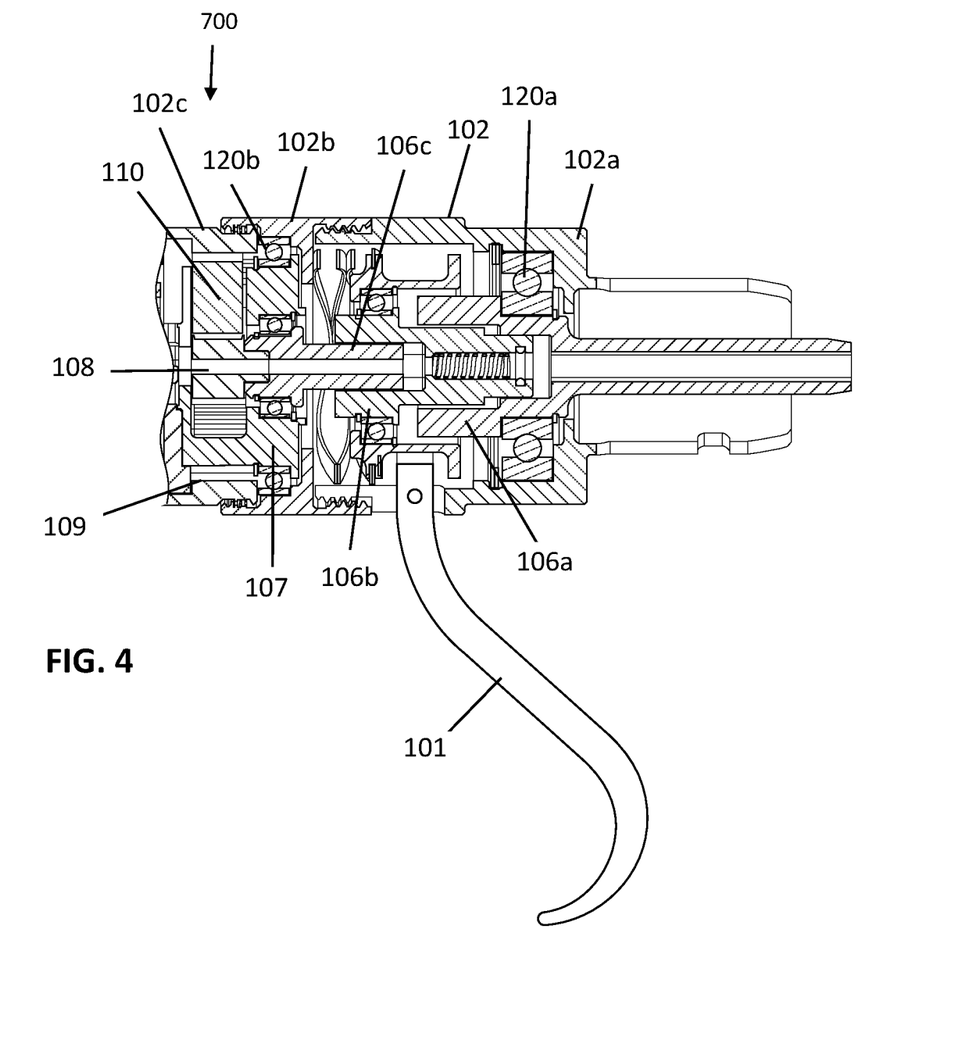
FIG. 4 shows a cross-sectional view of a speed reducing unit of the power module shown in FIG. 2, according to embodiments of the disclosure.
Figure 5:
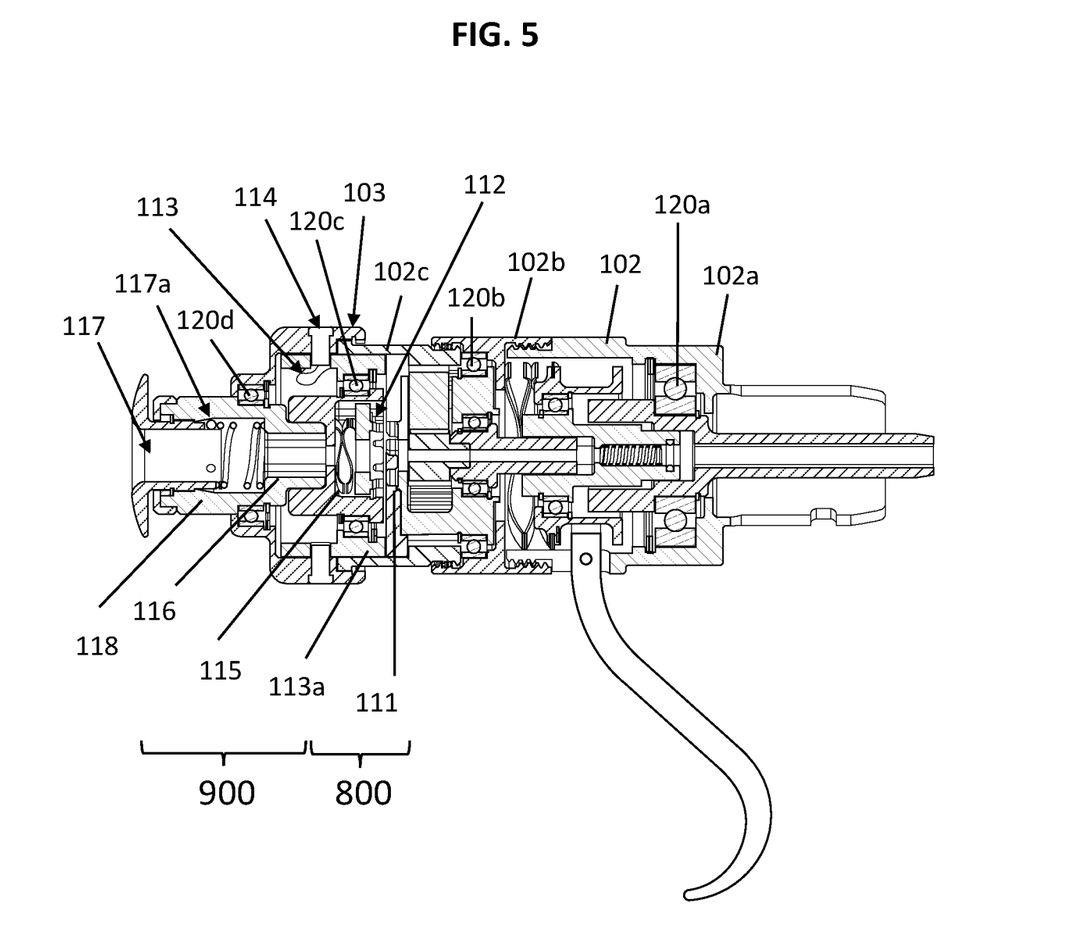
FIG. 5 shows a cross-sectional view of a drive mode switch unit and a quick connect unit of the power module shown in FIG. 2, according to embodiments of the disclosure.

Bearings may further be disposed between cover 102 and internal units of power module 100, e.g., units 600, 700, 800, and/or 900 to provide and maintain axial stability, prevent wobble during use of power module 100, and to maintain the connection and alignment of the components relative to one another in the manner described herein. For example, in the embodiment shown in FIGS. 2 and 3A, first bearing 120a may be disposed between cover 102 and components of stylet management unit 600. More particularly, first bearing 120a may be disposed between first cover component 102a and driveshaft 106, e.g., first driveshaft member 106a. As shown in FIGS. 2 and 4, second bearing 120b may be disposed between cover 102 and components of speed reducing unit 700. More particularly, second bearing 120b may be disposed between second cover component 102b and gear carrier 107. Still further, as shown in FIGS. 2 and 5, third bearing 120c may be disposed between cover 102 and components of drive mode switch unit 800, while fourth bearing 120d may be disposed between cover 102 and components of drive mode switch unit 800 and/or quick connect unit 900, e.g., between distal cap 103 and shaft 118, respectively.

Figure 3A:
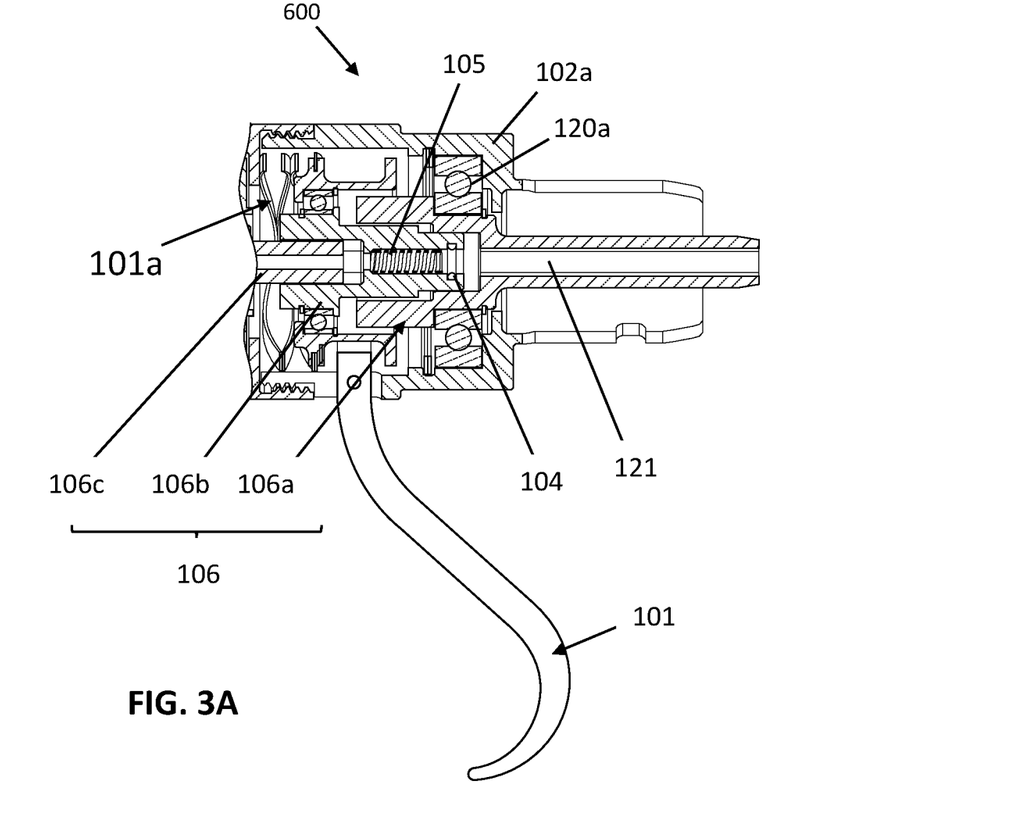
FIG. 3A shows a cross-sectional view of a stylet management unit of the power module shown in FIG. 2, according to embodiments of the disclosure.

FIG. 3A illustrates certain features of stylet management unit 600 of power module 100 (FIG. 1). As described with respect to FIG. 1, stylet management unit 600 is configured to lock stylet 200 to power module 100, to advance or retract stylet 200 relative to power module 100, and to remove stylet 200 from power module 100. Stylet management unit 600 may include a telescopic driveshaft 106 including two or more driveshaft members 106a, 106b, and so on. As illustrated in FIG. 3A, telescopic driveshaft 106 may include first driveshaft member 106a, second driveshaft member 106b, and third driveshaft member 106c. However, it is to be understood that driveshaft 106 can include any number of driveshaft members 106a, 106b, and so on, without departing from the disclosure. The driveshaft members 106a, 106b, 106c of driveshaft 106 may each include a cannulation 121 disposed through each member, configured to provide a continuous cannula when assembled, the cannula 121 being configured to accept insertion of stylet 200.

Stylet 200 may be configured and shaped to include a non-circular cross-sectional geometry at a proximal end thereof. For example, a proximal portion or end of stylet 200 may have a cross-sectional shape that is square, rectangular, hexagonal, star-shaped, or otherwise non-circular as is known in the art. Cannulation 121 in driveshaft members 106a, 106b, 106c, and so on, may have a complementary non-circular cross sectional shape. In particular, in some cases, stylet 200 (FIGS. 1 and 3B) may include a male cross sectional geometry at its proximal portion e.g., a square or hexagonal cross-section, that mates with and/or has a complementary fit with the female cross sectional geometry of cannulation 121 through telescopic driveshaft 106. This may facilitate rotational fixation of stylet 200 to driveshaft 106 when coupled thereto.

Figure 3B:
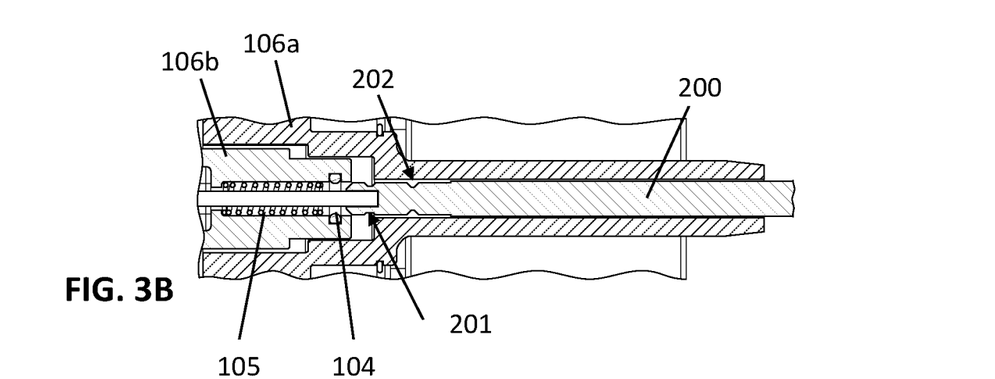
FIG. 3B shows an enlarged cross-sectional view of a portion of a stylet disposed within the stylet management unit of FIG. 3A, according to embodiments of the disclosure.

When the power module 100 (FIG. 1) is driven under power, e.g., by power hand piece 400 (FIG. 1), stylet 200 may be configured to spin, i.e. rotate, in the direction and at the speed output by power hand piece 400. Energy biasing element 104 (FIGS. 3A-3B), which may be, e.g., a canted coil spring, may be used to engage groove 201 (FIG. 3B) on stylet 200 to lock stylet 200 to second driveshaft member 106b. Alternatively, stylet 200 can include more than one groove such that energy biasing element 104 may engage with more than one groove on stylet 200. For example, as shown in FIG. 3B, stylet 200 may include first groove 201 and second groove 202 that is positioned proximal to first groove 201. In this example, loading stylet 200 using first groove 201 may create a lock from tension loading. To remove stylet 200, the user can push stylet 200 distally to reach second groove 202 that is located proximally relative to first groove 201 to reorient energy biasing element 104 and allow for easy removal in a proximal direction. As shown in the embodiment illustrated in FIG. 3B, stylet 200 may include a k-wire coupled to a proximal end connection, e.g., via welding, and grooves 201 and 202, if present, may be disposed on the proximal portion of stylet 200 coupled to the k-wire. Thus, stylet 200 facilitates rotational coupling between the k-wire and driveshaft 106, as further described below.

Stylet 200 can be loaded into lumen or cannulation 121 of telescopic driveshaft 106 to allow for control of stylet 200 for extension and retraction. Second driveshaft member 106b is configured to be translatable relative to first driveshaft member 106a and third driveshaft member 106c, while first driveshaft member 106a and third driveshaft member 106c are translationally fixed to cover 102, e.g., via retaining rings and radial bearings. Telescopic drive shaft 106 may be configured to be rotatable relative to cover 102 of power module 100 (FIG. 1). Telescopic driveshaft 106 and stylet 200, which are rotationally constrained relative to one another, are configured to rotate at the output speed of power hand piece 400 (FIG. 1), which may be, e.g., about 1500 revolutions per minute (RPM). Stylet trigger 101 can be configured to connect to second drive shaft member 106b such that pulling trigger 101 in a proximal direction causes second drive shaft member 106b to translate distally relative to the first driveshaft member 106a and third driveshaft member 106c, thereby allowing stylet 200 to advance distally.

With continued reference to FIG. 3A, stylet management unit 600 may include energy biasing element 105, which may be, e.g., a compression spring. Energy biasing element 105 may be disposed within the lumen or cannulation 121 of second driveshaft member 106b. Energy biasing element 105 may provide tactile feedback and/or audio feedback to the user when the user releases the connection between stylet 200 and power module 100. Another biasing element 101a, which may be, e.g., a wave spring, may be disposed within the lumen of cover 102. Biasing element 101a may be biased in a manner configured to restore trigger 101 back to its resting position, as shown in FIG. 2.

With reference to FIG. 4, features of speed reducing unit 700 of power module 100 (FIG. 1) are illustrated. Speed reducing unit 700 is configured to reduce the speed of the driveshaft and to output rotational motion at a decreased speed, e.g., to screw driver 300 (FIG. 1). Speed reducing unit 700 may be disposed distally relative to stylet management unit 600, and may include a planetary gear system configured to perform these functions. In particular, speed reducing unit 700 may include sun gear 108 at a proximal end thereof, configured to be coupled to a distal end of third driveshaft member 106c of stylet management unit 600 (FIG. 3A). Sun gear 108 is configured to rotate at a same speed of the third driveshaft member 106c, and thus, at the output speed of power hand piece 400 (FIG. 1). Gear carrier 107 may be configured to couple to sun gear 108 and rotate at a second speed that is slower than that of sun gear 108, according to a corresponding gear ratio. Such a gear ratio may be, e.g., 5:1 in certain embodiments. Gear carrier 107 may hold one or more planet gears 110, and the rotational axis of planet gears 110 may be fixed on gear carrier 107. The one or more planet gears 110 may also rotate at a speed identical to that of sun gear 108. Planet gears 110 can rotate on ring gear 109 on an inner surface of cover 102. In one particular embodiment, speed reducing unit 700 includes three planet gears 110 that are evenly spaced or distributed about sun gear 108, with sun gear 108 disposed in the center. Gear carrier 107 may include a cross sectional shape that is substantially circular.

With reference to FIG. 5, features of drive mode switch unit 800 are illustrated. Drive mode switch unit 800 is configured to switch between a first, stylet advancement mode and a second, screw mode, and for actuation of the drive clutch and driver. In some embodiments, drive mode switch unit 800 may include a distal cap 103 that is configured to be movable by a user between modes. While described herein as a cap, distal cap 103 may also be considered to be a knob or other similar structure. Distal cap 103 may be translationally, but not rotationally fixed to cover 102.

Distal cap 103 may include features which facilitate its engagement with a matching clutch 112. For example, distal cap 103 may include one or more helical slots 113 extending radially inward. A pin 114 may be present within each of the one or more helical slots 113, and may be configured to extend radially inward within its corresponding slot 113. Each pin 114 may further be configured to travel within the corresponding helical pin slot 113 on a pusher 113*a* when distal cap 103 is rotated by the user. Pusher 113*a* may be configured to be translationally fixed to matching clutch 112.

When distal cap 103 is rotated by a user in a first direction, e.g., clockwise or counter clockwise, to the screw mode position, the rotation causes translation of pusher 113*a* and matching clutch 112 in a proximal direction relative to cover 102, so that matching clutch 112 engages with drive clutch 111 at the distal end of gear carrier 107 (FIG. 4). Energy biasing element 115, which may be, e.g., a wave spring, may be configured to bias matching clutch 112 to engage with drive clutch 111. When this engagement occurs, matching clutch 112 may be configured to rotate in the same direction and at the same speed as drive clutch 111 and gear carrier 107, thereby also rotating screwdriver 300 (FIG. 1) in the same direction and at the same speed, due to the rotationally fixed relationship between matching clutch 112 and each of gear carrier 107 and driver 300. In this manner, bone anchor 500 (FIGS. 6A-6E) may be coupled to the distal end of screw driver 300, and may be inserted under the screw mode.

When distal cap 103 is rotated in the second, opposite direction from that of screw mode as described above, e.g., the other of the clockwise or counterclockwise direction, the rotation of pin 114 and translation of pusher 113*a* is configured to move matching clutch 112 distally so that matching clutch 112 disengages from drive clutch 111. As a result, screwdriver 300 disengages from power hand piece 400 (FIG. 1), and rotation and insertion of the screw stop.

With further reference to FIG. 5, power module 100 may include a quick connect unit 900 configured to couple a proximal end of driver 300 to power module 100. Quick connect unit 900 may comprise plunger 117 and pocket 116 configured to mate with a corresponding feature of screwdriver 300 at a proximal end thereof. Pocket 116 is rotationally fixed to pusher 113*a* and matching clutch 112. Pocket 116 may be square in shape, and may particularly be a 0.25 inch square pocket in certain embodiments. However, other geometries and sizes may also be used. Ball bearings and a mating female feature, e.g., mating female square feature, may be used to allow coupling to quick connect unit 900. Plunger 117 may include ramped geometry to push ball bearings 117*a* out, providing an interference fit with shaft 118. Pocket 116 may be configured to mate with a proximal portion of screwdriver 300, and to maintain engagement with the clutch mechanism via saddle joint(s).

Figure 6A:
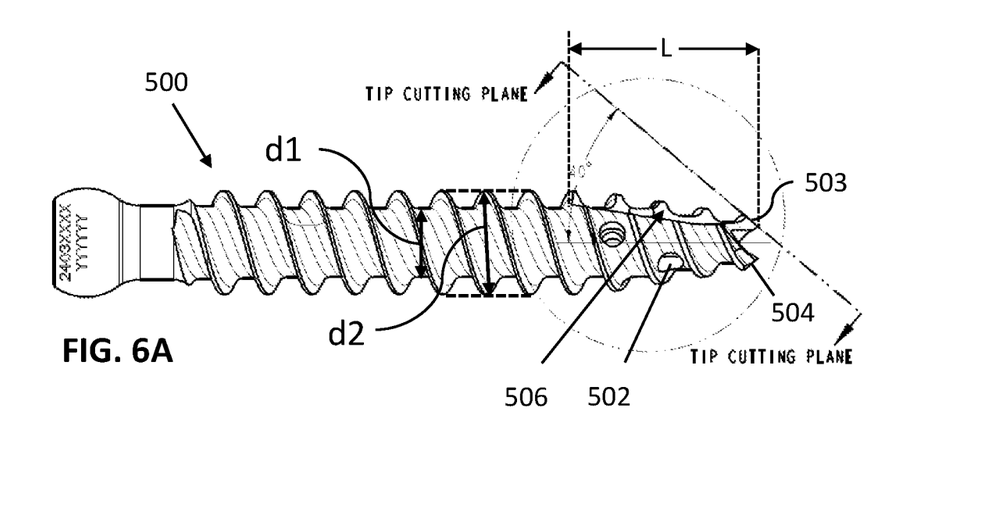
FIG. 6A shows a perspective view of aspects of a bone anchor, according to embodiments of the disclosure.
Figure 6B:
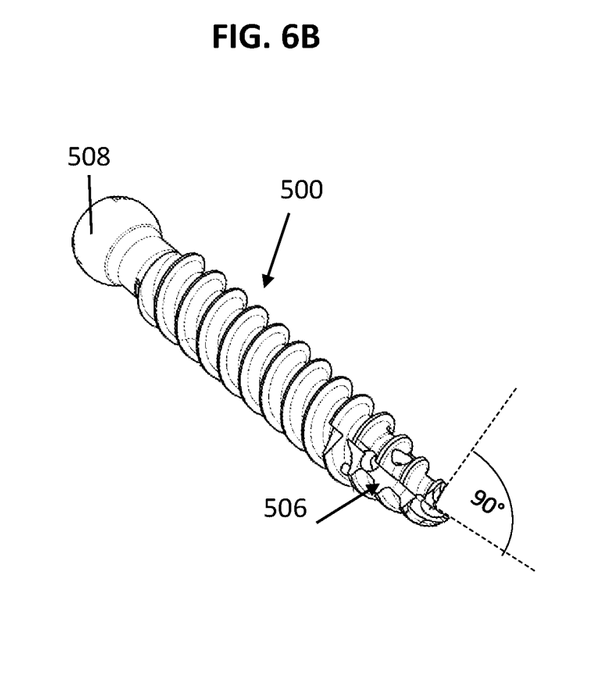
FIG. 6B shows a perspective view of aspects of a bone anchor, according to embodiments of the disclosure.
Figure 6C:
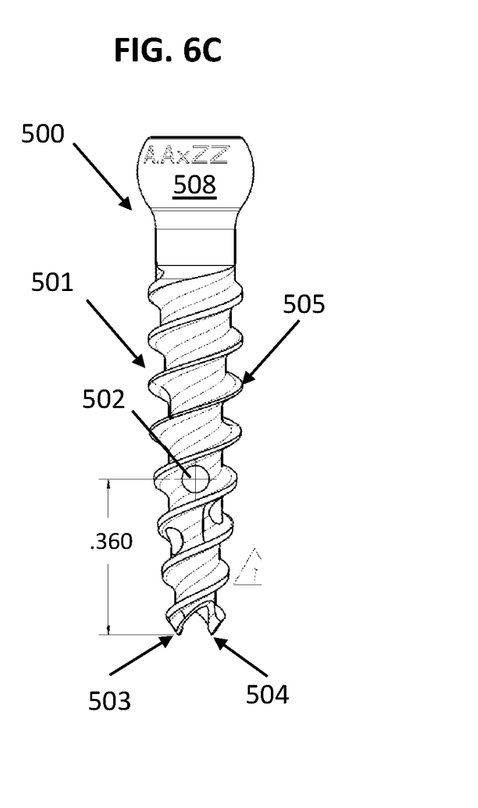
FIG. 6C shows a side view of aspects of a bone anchor, according to embodiments of the disclosure.

With reference to FIGS. 1-5, further details of the stylet advancement mode will now be described. In the stylet advancement mode, power module 100 is configured to cause advancement of stylet 200 into bone. In this mode, stylet 200 can be inserted from the proximal end of power module 100 and be rotationally locked in place by stylet management unit 600. When locked, stylet 200 is configured to rotate at the output speed and torque of power hand piece 400. Stylet 200 may be used to facilitate bone preparation for insertion of bone anchor 500 (FIGS. 6A-6E). The output speed may be, e.g., up to about 1500 rpm, and the output torque may be, e.g., about 20 inch-pounds (in.-lb.). Trigger 101 is configured to be pulled proximally to extend the locked stylet 200 distally beyond the tip of bone anchor 500, e.g., beyond cuts 503, 504 (FIG. 6A, 6C). When the trigger is released, stylet 200 retracts back to its original position proximal to the distal tip of the bone anchor 500, e.g., proximal relative to cuts 503, 504.

Still referring to FIGS. 1-5, in the screw mode, power module 100 is configured to advance bone anchor 500 (FIGS. 6A-6E) into bone. To switch from stylet advancement mode to screw mode, distal cap 103 may be rotated in the first direction as described above, until tactile and/or audio feedback is generated by power module 100.

Figure 11A:
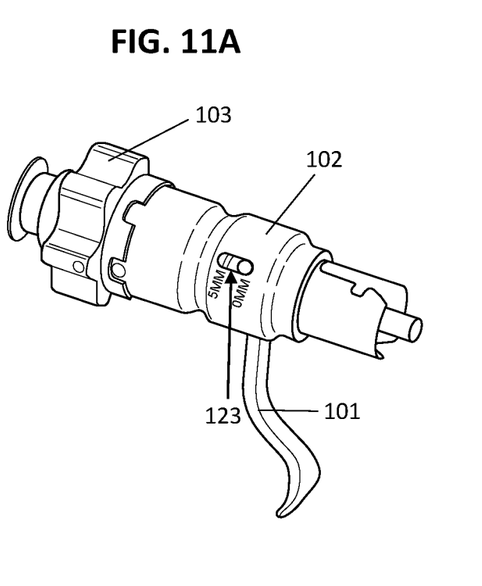
FIGS. 11A-11B show perspective views of portions of power module 100 of FIG. 2, including visual indicators according to embodiments of the disclosure.
Figure 11B:
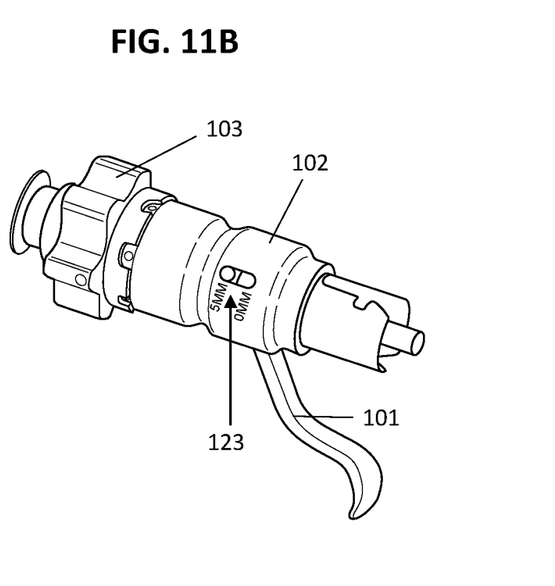

As shown in FIGS. 11A-11B, a visual indicator 123 may be included on an exterior of cover 102, such that a user can easily visually determine the current mode and whether stylet 200 is extended or retracted. FIG. 11A illustrates an exemplary indicator in a position indicating that stylet 200 is retracted, and screw mode is off, while FIG. 11B illustrates an exemplary indicator in a position indicating that stylet 200 is extended, and screw mode is on.

In the screw mode, the output speed of power hand piece 400 is configured to drive rotation of driveshaft 106 simultaneously. Speed reducing unit 700, through the coupled engagement of drive clutch 111 and matching clutch 112, is configured to reduce the speed at driveshaft 106 to a lower speed and a greater torque. The particular lower speed may be predetermined by the gear ratio of planetary gears 110, gear carrier 107, sun gear 108, and ring gear 109. The predetermined lower speed is the speed at which screw driver 300 rotates, therefore rotating bone anchor 500 at a lower speed than power hand piece 400, but with greater torque to facilitate insertion. For example, in the screw mode, driver 300 may rotate at a speed of, e.g., about 300 rpm, with a torque of, e.g., 100 inch-pounds, according to an exemplary 5:1 gear ratio.

FIGS. 6A-6E illustrate exemplary embodiments of bone anchor 500 for use as described herein. As illustrated, bone anchor 500 may include shank 501 with a trauma tip. In certain embodiments, bone anchor 500 may include a shank 501 (FIG. 6C) that is customized for a straight to screw insertion, advantageously eliminating the need for any pedicle preparation. The geometry of shank 501 at its distal end can be customized to minimize skiving and allow for immediate bone engagement, self-tapping, and self-starting.

Figure 6D:
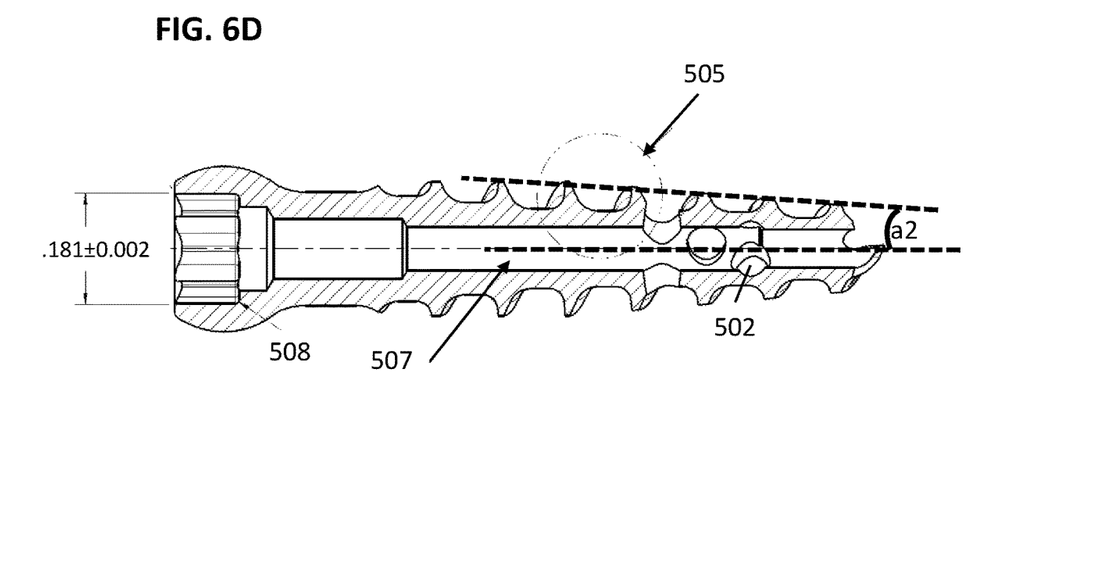
FIG. 6D shows a cross sectional view of aspects of a bone anchor, according to embodiments of the disclosure.
Figure 6E:
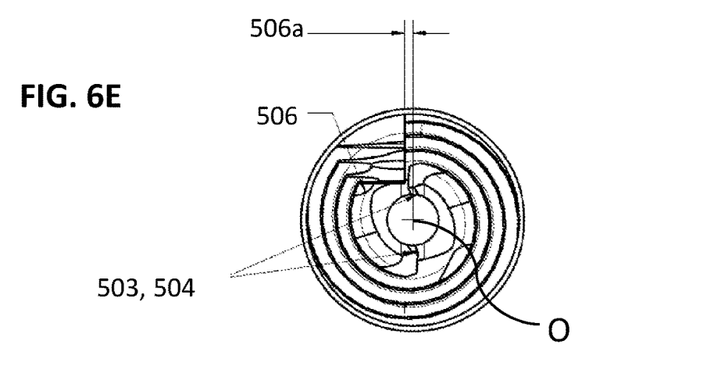
FIG. 6E shows a top view of aspects of a bone anchor, as viewed from the distal tip thereof, according to embodiments of the disclosure.

Shank 501 may include a cannulation 507 (FIG. 6D) for inserting stylet 200 (FIG. 1) or k-wire therein. In some embodiments, shank 501 is used for cancellous bone. Shank 501 may include a dual-lead thread form 505. In certain embodiments, the thread form may have a pitch of, e.g., about 0.108 inches, and a lead of, e.g., about 0.216 inches. Shank 501 may include two cuts 503, 504 at the distal end or tip of shank 501. Cuts 503, 504 may be on a cut plane as shown in FIG. 6A; the cutting plane may be at an angle in the range of about 25 to about 45 degrees, about 30 to about 40 degrees, or about 35 or 45 degrees in various embodiments. In the particular embodiment depicted in FIG. 6A, cuts 503, 504 may be on a 30 or 40 degree cut plane as shown in FIG. 6A. In some embodiments, one or two cutting flutes 506 (FIGS. 6A-6B) may be included on shank 501 to enable self-tapping and/or self-starting. Shank 501 may further include one or more through holes 502 (FIGS. 6A, 6C, 6D). In some embodiments, flute 506 and tip cuts 503, 504 are both clocked with the thread 505 starts of shank 501 as shown in FIG. 6E. Flute 506 may run out to just past where the major diameter starts, as shown in FIGS. 6A-6B and FIG. 6E, to allow for material relief and self-tapping as more material is displaced. In certain embodiments, one or more flutes 506 may have an offset 506a of about 0.1 inches from the central axis, O (FIG. 6E), of shank 501. Cutting flute(s) 506 can be clocked with the thread 505 start, and the two tip cuts 503, 504 can be clocked with thread 505 start, as also shown in FIG. 6E. The two cutting tips 503, 504 may be disposed in opposing relationship to each other.

The one or two flutes 506 may include a length, L (FIG. 6A), extending from the distal tip toward the proximal end of shank 501. Length L may be, e.g., within the range of 0.3 inches to 0.6 inches, within the range of 0.4 inches to 0.5 inches, or about 0.435 inches. In further embodiments, the distance between the two cutting tips 503, 504 (FIG. 6C) may be, e.g., about 0.10 inch, about 0.09 inch, about 0.08 inch, about 0.07 inch, or about 0.06 inch. Further, the head 508 (FIG. 6B) of bone anchor 500 may have a shape that is substantially spherical, and may have a diameter of, e.g., about 0.269 inch. One or more through-holes 502 may be present in shank 501, e.g., three through holes 502 may be present. In certain embodiments, one through hole 502 may be spaced a predetermined distance from the distal tip of bone anchor 500, e.g., about 0.36 inch from the distal tip of shank 501, about 0.288 inch from the distal tip of shank 501, or about 0.216 inch from the distal tip of shank 501.

As can be seen in FIGS. 6A-6D, the diameter of the minor profile, d1 (FIG. 6A) can be constant or tapered, and may be in the range of about 0.123 to about 0.300 inches. The diameter of the major profile, d2 (FIG. 6A), may be constant or tapered, and may be in the range of about 0.185 to about 0.415 inches. The taper angle a2 (FIG. 6D) can be about 5 degrees to about 20 degrees. The length of bone anchor 500 from proximal end to distal end can be about 1.348 to about 4.160 inches. It is noted, however, that the foregoing measurements describe certain exemplary embodiments, and are not considered to limit the disclosure in any way. Bone anchors 500 having dimensions and angles outside the particular ranges described herein may also be inserted according to the methods and devices described herein.

Figure 7:
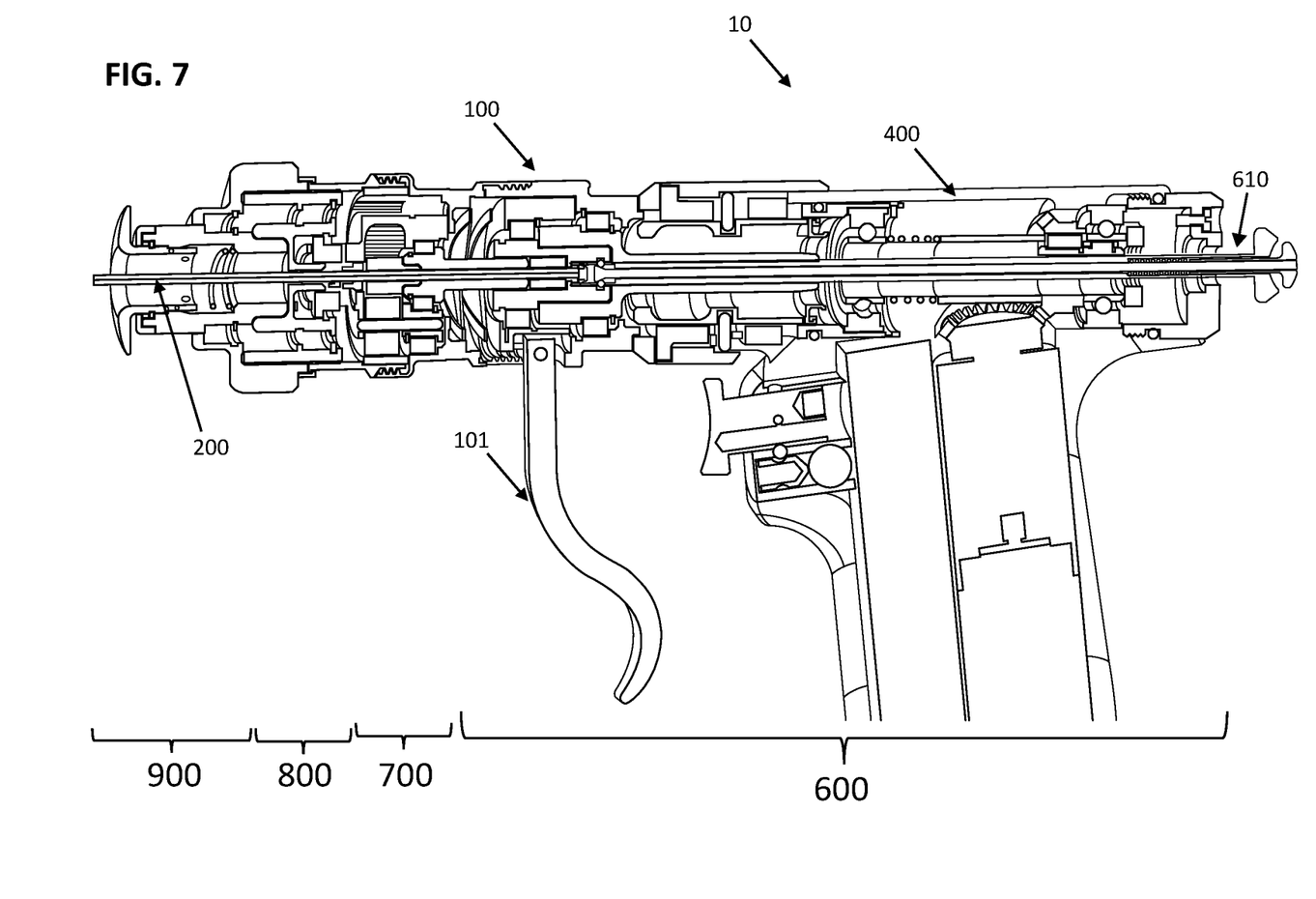
FIG. 7 shows a cross-sectional view of a power module coupled to a power hand piece, a stylet, and a screwdriver, according to embodiments of the disclosure.

FIG. 7 provides a cross-sectional view of a system 10 for bone anchor insertion according to an exemplary embodiment of the present disclosure. FIG. 7 depicts power module 100 connected with power hand piece 400. As shown, power module 100 includes stylet management unit 600, speed reducing unit 700, drive mode switch unit 800, and quick connect unit 900, as described above.

Figure 8:
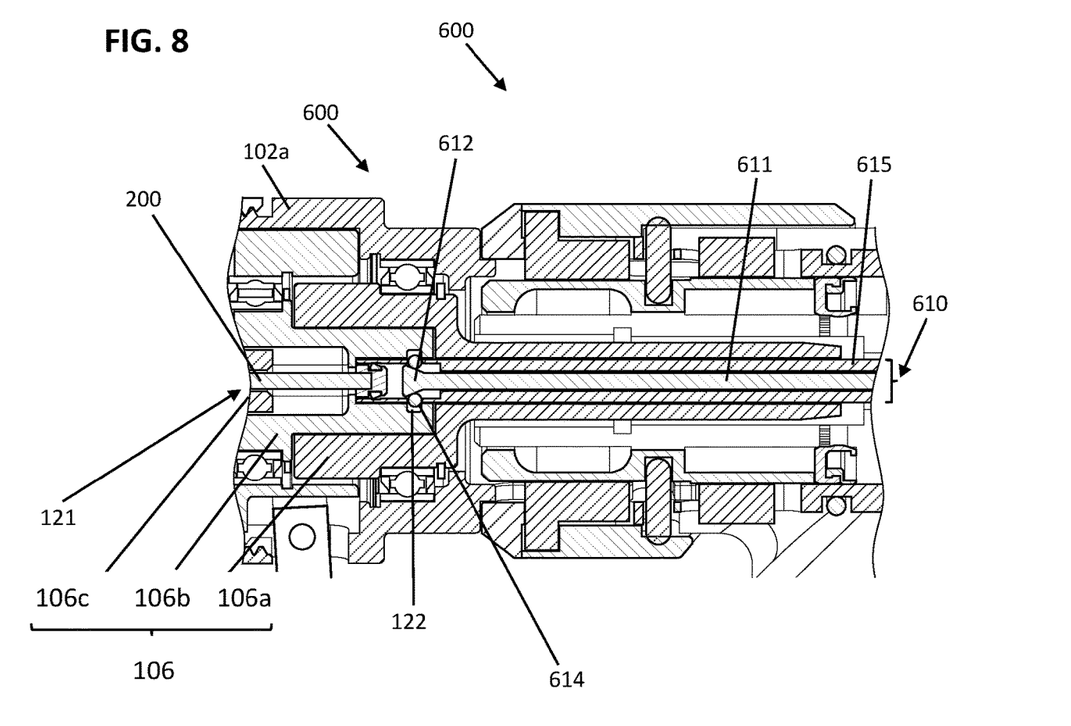
FIG. 8 shows an enlarged cross-sectional view of a stylet management unit of the power module shown in FIG. 7, according to embodiments of the disclosure.

FIG. 8 shows an enlarged cross-sectional view of portions of stylet management unit 600 as shown in FIG. 7. Stylet management unit 600 is configured to lock stylet 200 to power module 100, to advance or retract stylet 200 relative to power module 100, and to unlock and remove stylet 200 from power module 100. Stylet management unit 600 may be configured to include telescopic driveshaft 106, as described herein. As shown, driveshaft 106 includes first driveshaft member 106a, a second driveshaft member 106b, and third driveshaft member 106c. However, it is to be understood that the driveshaft 106 may be configured to include any number of driveshaft members without departing from the disclosure. A cannulation 121 having a first cross-sectional geometric shape can be provided within each driveshaft member 106a, 106b, 106c. In some cases, stylet 200 (FIGS. 1 and 7) may include a cross sectional geometric shape at its proximal portion that is non-circular and that mates with and/or is complementary to the geometric shape of cannulation 121 through the telescopic driveshaft 106 so that stylet 200 can be rotationally constrained relative to driveshaft 106. Exemplary shapes may include square, hexagon, and other shapes as is known in the art. When power module 100 (FIGS. 1 and 7) is driven under power by power hand piece 400 (FIGS. 1 and 7), stylet 200 is configured to spin in the same direction and at the same speed output by power hand piece 400.

Stylet 200 is configured to be loaded into telescopic driveshaft 106 to allow control of stylet 200 for extension and retraction. As discussed above, telescopic driveshaft 106 is cannulated, with a lumen 121 that allows insertion of stylet 200 therein. Second drive shaft member 106b is configured to translate relative to first driveshaft member 106a and third driveshaft member 106c, but first and third driveshaft members 106a, 106c are configured to be translationally fixed relative to cover 102 (FIG. 2), e.g., via retaining rings and radial bearings. Telescopic driveshaft 106 is configured to rotate relative to cover 102 of power module 100 (FIGS. 1 and 7). The rotational speed of telescopic driveshaft 106 is configured to be identical to the output speed of power hand piece 400 (FIGS. 1 and 7), and may be, e.g., about 1500 revolutions per minute (rpm). The rotational speed is configured to be identical to that of stylet 200 as well, since stylet 200 and telescopic driveshaft 106 are rotationally constrained relative to each other. Stylet trigger 101 (FIG. 7) is configured to be coupled to second drive shaft member 106b such that pulling trigger 101 proximally causes second drive shaft member 106b to translate distally relative to first and third driveshaft members 106a, 106c, thereby allowing stylet 200 to advance distally.

Figures 9A, 9B:
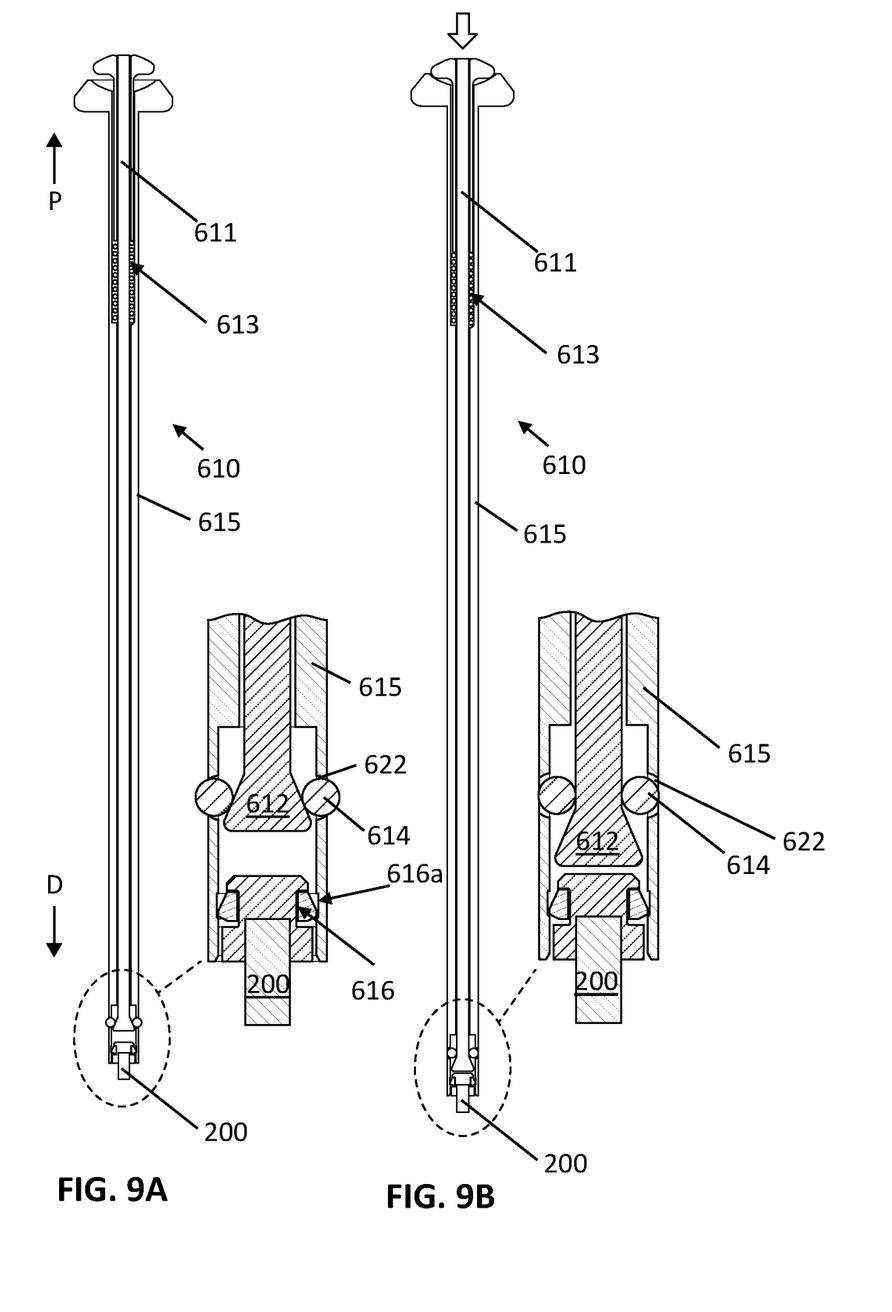
FIG. 9A shows a cross sectional view of aspects of the stylet management unit in FIG. 8, including a quick connect feature, in a connected state according to embodiments of the disclosure.
FIG. 9B shows cross sectional view of aspects of the stylet management unit in FIGS. 8 and 9A, including a quick connect feature in a disconnected state, according to embodiments of the disclosure.
Figure 10:
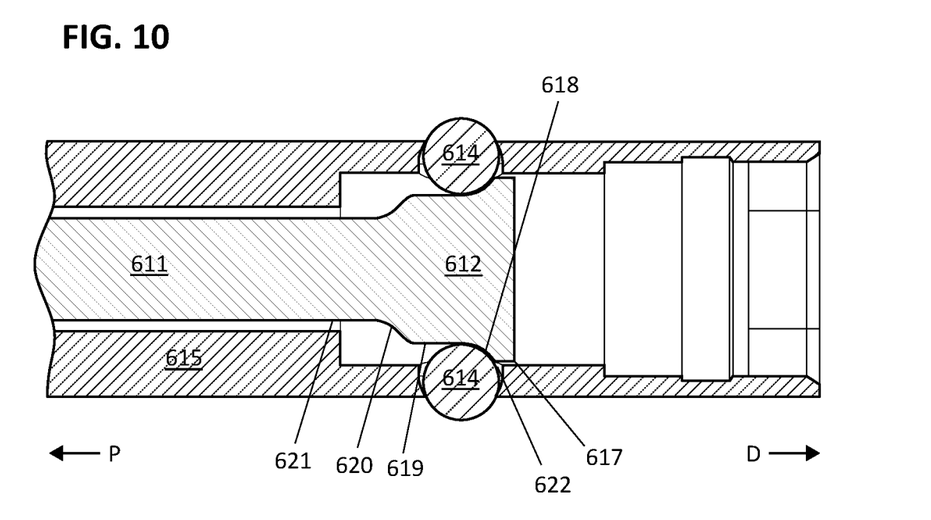
FIG. 10 shows an enlarged cross-sectional view of aspects of the stylet management unit in FIG. 8, according to embodiments of the disclosure.

FIGS. 9A-9B illustrate details of one embodiment of a connection between power module 100 and power hand piece 400, in the form of quick connect feature 610 of stylet management unit 600. Quick connect feature 610 as described herein may be used, for example, in lieu of grooves 201, 202 (FIG. 3B) to couple stylet 200 to stylet management unit 600 (FIG. 3A). FIG. 9A shows aspects of the device in a connected condition or position, in which quick connect feature 610 is configured to connect power module 100 to power hand piece 400. FIG. 9B shows aspects of the device in a disconnected condition or position, in which quick connect feature 610 is disconnected from power hand piece 400. Quick connect feature 610 may include outer shaft 615, having a lumen disposed therein, and inner shaft 611 disposed within the lumen of outer shaft 615. Inner shaft 611 has a tapered distal end 612, as shown in, e.g., FIGS. 9A-9B and FIG. 10. Tapered distal end 612 has a diameter that is widest at its distal end, and tapers or transitions to a smaller diameter moving proximally away from the distal end. The majority of the length of inner shaft 611 is proximal of the tapered distal end 612, and has a constant, or substantially constant, and smaller outer diameter 621 (FIG. 10). Energy biasing element 613 is configured to bias inner shaft 611 toward the proximal end, and may be, e.g., a coil spring disposed about inner shaft 611.

One or more ball bearings 614 may be disposed within the lumen in outer shaft 615, and may be positioned proximal to at least a portion of tapered distal end 612 of inner shaft 611, such that when inner shaft 611 is moved proximally within outer shaft 615, ball bearings 614 are carried proximally as well by a larger diameter tapered or shoulder surface of tapered distal end 612. One or more grooves 622 in outer shaft 615 may be provided, in which ball bearings 614 rest in the position shown in FIG. 9A. Grooves 622 are configured to allow ball bearings 614 to extend radially outward beyond an outer surface of outer shaft 615.

Corresponding grooves 122 may be provided on an inner surface of cannula 121 in second driveshaft member 106b (FIG. 8). Ball bearings 614 may be configured to engage with corresponding grooves 122 in second driveshaft member 106b when ball bearings 614 are at rest in grooves 622 and extending outwardly from outer shaft 615. When inner shaft 611 is pushed distally against the force of biasing element 613, as shown in FIG. 9B, distal end 612 of inner shaft 611 translates distally. As tapered distal end 612 translates distally, this allows ball bearings 614 to travel out of grooves 622 in a radially inward direction along the tapered or shoulder surface of tapered distal end 612 toward inner shaft 611. As a result of this motion, ball bearings 614 no longer extend outwardly from outer shaft 615, and are removed from engagement with grooves 122 in second driveshaft member 106b. This configuration allows disassociation of ball bearings 614 with respect to grooves 122, as ball bearings 614 are contained within outer shaft 615. Power module 100 may then disconnect from power hand piece 400.

When inner shaft 611 is not pushed, urged, or moved distally under force, or is at its proximal resting position as shown in FIG. 9A, tapered distal end 612 may push ball bearings 614 outward such that ball bearings 614 extend beyond outer shaft 615, through grooves 622 as shown in FIG. 9A. The portion of each ball bearings 614 that extends outside of outer shaft 615 through groove 622 is configured to engage with groove 122 in driveshaft member 106b. In this position, quick connect feature 610 enables connection to power hand piece 400. Stylet 200 can be quickly attached to power module 100 with a tapered retention clip 616, which may couple to or disengage from the matching element 616a of outer shaft 615. Inserting stylet 200 may require a smaller force than the force to remove stylet 200 due to the shape and size of tapered retention clip 616, which advantageously ensures safe and secure attachment of stylet 200 to power module 100.

The embodiment of FIG. 10 is similar to that of FIGS. 9A-9B, but depicts another possible geometry of tapered end 612 of inner shaft 611. In the embodiment of FIG. 10, like that of FIGS. 9A-9B, tapered end 612 has a first diameter 617 at its distal most end, that is larger than the diameter 621 of inner shaft 611 and larger than the diameter of any point along the taper. However, rather than a continuous taper from the larger distal end diameter to the smaller inner shaft diameter (FIGS. 9A-9B), tapered distal end 612 includes one or more changes in its diameter and geometry. In the embodiment of FIG. 10, a first shoulder 618 is provided proximal of first diameter 617, providing a curved surface having a radius of curvature that complements a curvature radius of ball bearing 614. Ball bearing 614 sits against complementary shoulder surface 618 in the connected position analogous to that shown in FIG. 9A. Along shoulder surface 618, the diameter transitions from first diameter 617 to second, smaller diameter 619. A second shoulder 620 is provided proximal of second diameter 619, providing a curved surface having a radius of curvature that complements a curvature radius of ball bearing 614. Ball bearing 614 sits against complementary shoulder surface 620 in a disconnected position analogous to that shown in FIG. 9B. Along shoulder surface 620, the diameter transitions from second, smaller diameter 619 to a third, still smaller diameter 621, which may be maintained extending proximally along a length of inner shaft 611.

Unless otherwise defined, all technical terms used herein have the same meaning as commonly understood by one of ordinary skill in the art to which this invention belongs. As used in this specification and the appended claims, the singular forms "a," "an," and "the" include plural references unless the context clearly dictates otherwise. Any reference to "or" herein is intended to encompass "and/or" unless otherwise stated. As used in this specification and the claims, unless otherwise stated, the term "about," "approximately," "generally," and "substantially" refers to variations of less than or equal to +/−1%, +/−2%, +/−3%, +/−4%, +/−5%, +/−6%, +/−7%, +/−8%, +/−9%, +/−10%, +/−11%, +/−12%, +/−14%, +/−15%, +/−16%, +/−17%, +/−18%, +/−19%, or +/−20%, depending on the embodiment. As a further non-limiting example, about 100 millimeters represents a range of 95 millimeters to 105 millimeters, 90 millimeters to 110 millimeters, or 85 millimeters to 115 millimeters, depending on the embodiments.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A power module configured for adjustably controlling insertion of a bone anchor and a stylet under power from a motor, the power module comprising:
   a driveshaft operatively coupled to the motor and configured to rotate at a first speed equal to a speed of rotation of the motor,
   a gear system couplable at a proximal end thereof to the driveshaft, and at a distal end thereof to a medical instrument, wherein:
      in a first mode of operation, the gear system is configured to be disengaged from the driveshaft, and
      in a second mode of operation, the gear system is configured to engage with the driveshaft, and to reduce the first speed of rotation of the driveshaft to a second speed of rotation that is lower than the first speed, wherein the medical instrument is configured to rotate at the second speed of rotation;
   a cover disposed over at least a portion of the power module, wherein the telescopic driveshaft is rotatable relative to the cover, and wherein the first driveshaft member and the third driveshaft member are translationally fixed relative to the cover, wherein the drive shaft comprises a cannula disposed within the driveshaft, the cannula being configured to engage the stylet within the cannula in the first mode of operation, thereby causing the stylet to rotate at the first speed of rotation, wherein each of the gear system and the medical instrument include an axially extending cannula through which at least a portion of the stylet extends, wherein the driveshaft comprises a telescopic driveshaft, and the telescopic driveshaft includes a first driveshaft member, a second driveshaft member, and a third driveshaft member, and wherein the gear system comprises a sun gear coupled to a distal end of the driveshaft, wherein the sun gear rotates at the first speed of rotation.

2. The power module of claim 1, wherein the second driveshaft member is translatable relative to the first driveshaft member and the third driveshaft member.

3. The power module of claim 2, further comprising a stylet trigger coupled to the second driveshaft member, wherein the stylet trigger is configured to cause translation of the second driveshaft member and the stylet in a distal direction relative to the first and the third driveshaft members.

4. The power module of claim 1, wherein the cover comprises a first cover component and a second cover component, and wherein the first cover component is affixed to the second cover component by a threaded connection, an adhesive, or a weld.

5. The power module of claim 1, wherein the gear system further comprises:
a gear carrier coupled with the sun gear and configured to rotate at a speed slower than the first speed;
one or more planet gears configured to be carried by the gear carrier and to rotate about an axis fixed on the gear carrier; and
a ring gear disposed about the gear carrier and the one or more planet gears, configured to engage with the one or more planet gears, wherein each of the one or more planet gears rotates at the slower speed on the ring gear on an inner surface of the cover.

6. The power module of claim 5, wherein the second speed is one-fifth (⅕) of the first speed.

7. The power module of claim 5, further comprising:
a first clutch coupled to the gear carrier; and
a second clutch configured to axially translate relative to the first clutch and to releasably engage with the first clutch,
wherein in the first mode of operation, the second clutch is configured to translate distally and to be disengaged from the first clutch, and
in the second mode of operation, the second clutch is configured to translate proximally and to engage with the first clutch, wherein the first clutch, the second clutch, the gear carrier, and the medical instrument are rotationally fixed to one another.

8. The power module of claim 7, further comprising a distal cap configured to actuate axial translation of the second clutch, thereby causing the power module to shift between the first mode of operation and the second mode of operation.

9. The power module of claim 8, wherein the distal cap is configured to be rotatable in a first direction, thereby causing the second clutch to translate distally and to disengage from the first clutch, and wherein the distal cap is rotatable in a second, opposite direction, thereby causing the second clutch to translate proximally and to engage with the first clutch.

10. The power module of claim 7, further comprising: a quick connect coupling configured to reversibly couple a proximal end of the medical instrument to the second clutch, wherein the medical instrument is rotationally fixed to the second clutch when the proximal end of the medical instrument is coupled to the second clutch.

11. The power module of claim 1, further comprising one or more bearings disposed between the cover and the gear system, or between the cover and the driveshaft.

12. The power module of claim 1, further configured to advance the stylet into bone in the first mode of operation.

13. The power module of claim 1, further configured to advance the bone anchor into bone in the second mode of operation.

14. The power module of claim 1, wherein the medical instrument is a screw driver.

15. A power module configured for inserting a bone anchor and a stylet under power from a motor, the power module comprising:
a telescopic driveshaft comprising a cannula therein, the cannula being configured to engage the stylet; and
a driver coupled to the telescopic driveshaft and configured to rotate in response to rotation of the telescopic driveshaft;
a quick connect feature configured to releasably couple the power module to a power handpiece comprising the motor, wherein the quick connect feature comprises:
an outer shaft having a lumen therein; and
an inner shaft disposed within the lumen of the outer shaft, wherein the inner shaft comprises a first diameter along a length of the inner shaft, a second, larger diameter at a distal end of the inner shaft, and a tapered portion from the first diameter to the second diameter;
wherein, in a connected position, a distal end of the outer shaft is configured to be inserted into the cannula and engage a portion of the telescopic driveshaft, and to engage a proximal end of the stylet; and
in a disconnected position, the distal end of the outer shaft is configured to disengage from the telescopic driveshaft and the proximal end of the stylet.

16. The power module of claim 15, further comprising:
a first groove disposed on an inner surface of the cannula within the telescopic driveshaft;
a corresponding groove in the outer shaft; and
at least one ball bearing disposed within the lumen of the outer shaft, adjacent the tapered portion of the inner shaft;
wherein, in the connected position, the at least one ball bearing extends radially outward through the second, corresponding groove in the outer shaft, into the first groove in the telescopic driveshaft, thereby locking the outer shaft in axial engagement with the telescopic driveshaft, and
wherein, in the disconnected position, the inner shaft is configured to translate in a distal direction, thereby causing the at least one ball bearing to move radially inward along the tapered portion and to exit the first groove and the second corresponding groove, thereby releasing the axial engagement of the outer shaft and the telescopic driveshaft.

17. The power module of claim 15, further comprising a tapered retention clip configured to releasably couple the proximal end of the stylet to a distal end of the outer shaft.

* * * * *